(12) United States Patent
Verrant et al.

(10) Patent No.: US 9,127,302 B2
(45) Date of Patent: Sep. 8, 2015

(54) SYSTEM FOR THE DETECTION AND ENUMERATION OF SUSPECT TARGET CELLS IN A MIXED CELL POPULATION

(75) Inventors: John A Verrant, Missing, PA (US); Arjan G. J. Tibbe, Deventer (NL); Brad Foulk, Chalfont, PA (US); Joost F. Swennenhuis, Eefide (NL); Leon W. M. M. Terstappen, Amsterdam (NL); Mark Carle Connelly, Doylestown, PA (US); Michael T. Kagan, Sebec, ME (US)

(73) Assignee: Janssen Diagnostics, LLC, Raritan, NJ (US)

( * ) Notice: Subject to any disclaimer, the term of this patent is extended or adjusted under 35 U.S.C. 154(b) by 856 days.

(21) Appl. No.: 12/067,532

(22) PCT Filed: Sep. 20, 2006

(86) PCT No.: PCT/US2006/036656
§ 371 (c)(1),
(2), (4) Date: Oct. 10, 2008

(87) PCT Pub. No.: WO2007/053245
PCT Pub. Date: May 10, 2007

(65) Prior Publication Data
US 2009/0220955 A1 Sep. 3, 2009

Related U.S. Application Data

(60) Provisional application No. 60/729,536, filed on Oct. 24, 2005, provisional application No. 60/786,117, filed on Mar. 27, 2006.

(51) Int. Cl.
| | |
|---|---|
| *C12Q 1/68* | (2006.01) |
| *G01N 33/53* | (2006.01) |
| *C12M 1/00* | (2006.01) |
| *C12M 1/34* | (2006.01) |
| *A61K 39/395* | (2006.01) |
| *C12Q 1/34* | (2006.01) |

(52) U.S. Cl.
CPC ................ *C12Q 1/34* (2013.01); *C12Q 1/6811* (2013.01); *C12Q 1/6876* (2013.01)

(58) Field of Classification Search
CPC .... C12Q 1/6813; C12Q 1/6827; G01N 33/53; C12M 1/00; C12M 1/34; C07H 21/00; C07H 21/02; C07H 21/04; A61K 39/00
USPC .................................... 435/6, 7.1, 283.1, 6.1
See application file for complete search history.

(56) References Cited

U.S. PATENT DOCUMENTS

| | | | | |
|---|---|---|---|---|
| 4,554,088 | A | * | 11/1985 | Whitehead et al. ........ 252/62.54 |
| 5,108,933 | A | * | 4/1992 | Liberti et al. ................ 436/501 |
| 5,466,574 | A | * | 11/1995 | Liberti et al. ..................... 435/5 |
| 5,821,066 | A | * | 10/1998 | Pyle et al. ..................... 435/7.2 |
| 6,150,173 | A | | 11/2000 | Schubert |
| 6,169,169 | B1 | * | 1/2001 | Hyldig-Nielsen et al. ... 536/22.1 |
| 6,365,362 | B1 | | 4/2002 | Terstappen et al. |
| 6,429,293 | B1 | | 8/2002 | Hew |
| 6,524,798 | B1 | * | 2/2003 | Goldbard et al. ............ 435/6.14 |
| 6,541,204 | B2 | | 4/2003 | Nilsen et al. |
| 2002/0098535 | A1 | | 7/2002 | Wang et al. |
| 2002/0109838 | A1 | | 8/2002 | Columbus |
| 2002/0172987 | A1 | | 11/2002 | Terstappen et al. |
| 2003/0082632 | A1 | | 5/2003 | Shumate |
| 2003/0119077 | A1 | | 6/2003 | Ts'o et al. |
| 2003/0124530 | A1 | | 7/2003 | Edwards et al. |
| 2003/0129626 | A1 | | 7/2003 | Nielsen et al. |
| 2004/0209298 | A1 | | 10/2004 | Kamberov et al. |
| 2005/0064450 | A1 | | 3/2005 | Lucas et al. |
| 2005/0164216 | A1 | | 7/2005 | Lukyanov et al. |

FOREIGN PATENT DOCUMENTS

| | | |
|---|---|---|
| CN | 1494552 A | 4/2006 |
| EP | 1722230 A2 | 11/2006 |
| JP | 2000508171 A | 10/1997 |
| JP | 2003527098 A | 3/2001 |
| JP | 2002-517183 A | 6/2002 |
| JP | 2005507997 A | 5/2003 |
| JP | 2005-524833 A | 8/2005 |
| JP | 2007-505626 A | 3/2007 |

(Continued)

OTHER PUBLICATIONS

Rauch et al., Quantitative microscopy after fluorescence in situ hybridization—a comparison between repeat-depleted and non-depleted DNA probes. Journal of Biochemical and Biophysical Methods 44 :59 (2000).*
Allard et al., Nonmalignant Diseases Carcinomas but not in Healthy Subjects or Patients With Tumor Cells Circulate in the Peripheral Blood of All Major. Clinical Cancer Research 10 :6897 (2004).*
Berois et al., Detection of rare human breast cancer cells. Comparison of an immunomagnetic separation method with immunocytochemistry and RT-PCR. Anticancer Research 17 :2639 (1997).*
Cuny et al., Relating Genotype and Phenotype in Breast Cancer: An Analysis of the Prognostic Significance of Amplification at Eight Different Genes or Loci and of p53 Mutations. Cancer Research 60 : 1077 (2000).*
Little et al., Genotype/Phenotype Analyses of Low Frequency Tumor Cells Using Computerized Image Microscopy. Cytometry 23 :344 (1996).*
Mao et al., Phenotype and Genotype of Advanced Premalignant Head and Neck Lesions After Chemopreventive Therapy. Journal of the National Cancer Institute 90 (20): 1550 (1998).*
Naume et al., Immunomagnetic Techniques for the Enrichment and Detection of Isolated Breast Carcinoma Cells in Bone Marrow and Peripheral Blood. Journal of Hematotherapy 6: 103-114 (1997).*
Berndt, Uta et al., "Systematic high-content proteomic analysis reveals substantial immunologic changes in colorectal cancer," Cancer Research, vol. 68, No. 3, Feb. 2008, pp. 880-888.

(Continued)

*Primary Examiner* — Ethan Whisenant

(57) ABSTRACT

The invention relates generally to the field of identification of DNA sequences, genes or chromosomes. Methods and composition to obtain Unique Sequence DNA probes are provided. Composition comprises of any double stranded DNA containing Unique Sequences from which the repetitive sequences are eliminated according to the method described in this invention. The invention also relates to the preservation of cells that have been identified after immunomagnetic selection and fluorescent labeling in order to further interrogate the cells of interest. Furthermore the invention relates to genetic analysis of cells that have been identified after immunomagnetic selection and fluorescent labeling.

4 Claims, 11 Drawing Sheets

(56) References Cited

FOREIGN PATENT DOCUMENTS

| JP | 2005522224 A | | 7/2009 |
|---|---|---|---|
| JP | 2005514062 A | | 11/2010 |
| WO | WO 01/06014 | | 1/2001 |
| WO | WO01/29253 | * | 4/2001 |
| WO | WO 2004/058404 A2 | | 7/2004 |
| WO | WO 2004/076643 A2 | | 9/2004 |
| WO | WO 2004/083386 | | 9/2004 |
| WO | WO 2007/053245 A2 | | 5/2007 |

OTHER PUBLICATIONS

Schubert, Walter et al., "Analyzing proteome topology and function by automated multidimensional fluorescence microscopy," Nature Biotechnology, Nature Publishing Group, NY, USA, vol. 24, No. 10, Oct. 2006, pp. 1270-1278.

Craig, J.M. et al., "Removal of Repetitive Sequcens from Fish Probes Using PCR-Assisted Affinity Chromatography," Human Genetics, Springer, Berlin, DE, vol. 100, Jan. 1997, pp. 472-476.

Davison, J.M. et al., "Technical advance. Subtracted unique sequence in situ hybridization experimental and diagnostic applications," American Journal of Pathology, American Society for Investigative Pathology, US, vol. 153, No. 5, Nov. 1998, pp. 1401-1409.

Anja Mittag et al., "Hyperchromatic cytometry principle for cytomics using a slide based cytometry" Cytometry Part A, 69A, No. 7, pp. 691-703 May 5, 2006.

Bonnekoh Bernd et al: "Profiling Lymphocyte Subpopulations in Peripheral Blood Under Efalizumab Treatment of Psoriasis by Multi Epitope Ligand Cartography (MELC) Robot Microscopy", European Journal of Dermatology, John Libbey Eurotext, FR, vol. 16, No. 6, Jan. 1, 2006, pp. 623-635, XP008079835, ISSN: 1167-1122.

* cited by examiner

SYSTEM FOR THE DETECTION AND ENUMERATION OF SUSPECT TARGET CELLS IN A MIXED CELL POPULATION

CROSS-REFERENCE TO RELATED APPLICATIONS

This is a non-provisional application which claims priority to U.S. Provisional Applications 60/713,676, filed 20 Sep. 2005; 60/729,536, filed 24 Oct. 2005; and 60/786,117, filed Mar. 2006. Each of the aforementioned applications is incorporated in full by reference herein.

BACKGROUND OF THE INVENTION

1. Field of the Invention

The invention relates generally to the field of identification of DNA sequences, genes or chromosomes.
Generation of DNA Probes Human genomic DNA is a mixture of unique sequences and repetitive sequences that are present in multiple copies throughout the genome. In some applications, nucleic acid hybridization probes to detect repetitive sequences are desirable. These probes have shown utility in the fields of fetal cell diagnostics, oncology, and cytogenetics. In other applications it is desirable to generate hybridization probes that anneal only to unique sequences of interest on a chromosome. Preparation of unique sequence probes is confounded by the presence of numerous classes of repetitive sequences throughout the genome of the organism (Hood et al., *Molecular Biology of Eucaryotic Cells* (Benjamin/Cummings Publishing Company, Menlo Park, Calif. 1975). The presence of repetitive sequences in hybridization probes will reduce the specificity of the probes because portions of the probe will bind to other repetitive sequences found outside the sequence of interest. Thus, to ensure binding of hybridization probes to a specific sequence of interest, efforts must be made to ensure that repetitive sequences ill the probe do not anneal to the target DNA outside the sequence of interest.

Recent contributions have addressed this question by inhibiting hybridization of the repetitive sequences with the use of unlabeled blocking nucleic acids (U.S. Pat. Nos. 5,447,841 and 6,596,479). Use of blocking nucleic acids in hybridizations is expensive, does not completely prevent hybridization of the repetitive sequences, and can distort genomic hybridization patterns (Newkirk et al., "Distortion of quantitative genomic and expression hybridization by Cot-1 DNA: mitigation of this effect," *Nucleic Acids Res*. vol 33 (22):e191 (2005)). Thus, methods that prevent hybridization of repeat sequences without the use of blocking DNA are necessary for optimal hybridization.

One means to achieve this is to remove unwanted repeat segments from the hybridization probes prior to hybridization. Techniques involving the removal of highly repetitive sequences have been previously described. Absorbents, like hydroxyapatite, provide a means to remove highly repetitive sequences from extracted DNA. Hyroxyapatite chromatography fractionates DNA on tie basis of duplex re-association conditions, such as temperature, salt concentration, or other stringencies. This procedure is cumbersome and varies with different sequences. Repeat DNA can also be removed by hybridization to immobilized DNA (Brison et al., "General Methods for Cloning Amplified DNA by Differential Screening with Genomic Probes," Molecular and Cellular Biology, Vol. 2, pp. 578-587 (1982)). In all of these procedures, the physical removal of the repetitive sequences will depend upon the strict optimization of conditions with inherent variations based upon the base composition of the DNA sequence.

Several other methods to remove repetitive sequences from hybridization probes have been described. One method involves using a cross-linking agent to cross-link repetitive sequences either to directly prevent hybridization of repetitive sequences or to prevent amplification of repeat sequences in a PCR reaction. (U.S. Pat. No. 6,406,850). Another method uses PCR assisted affinity chromatography to remove repeats from hybridization probes (U.S. Pat. No. 6,569,621). Both of these methods rely on the use of labeled DNA to remove repeat sequences which makes these processes complex and difficult to reproduce. Further, both methods are time consuming, requiring multiple rounds of repeat removal to produce functional probes, suitable for use in fluorescent in situ hybridization (FISH) or other hybridization reactions requiring high target specificity.

The use of duplex specific nucleases which preferentially cleave double stranded deoxyribonucleic acid molecules has been described for sequence variant detection applications such as single nucleotide polymorphisms (US 2005/0164216; U.S. Pat. No. 6,541,204). The ability of the enzyme to preferentially cleave perfectly matched nucleic acid duplex polynucleotides as compared to single stranded provides a means for removing non-target double stranded DNA from the sample mixture.

The ability of these nucleases to specifically digest the duplex form of polynucleotides was discovered in the instant invention to provide substantial benefit in manufacturing unique target specific probes that do not require blocking DNA, thus eliminating the costs and interfering affect of blocking DNA, and providing a means for rapid, efficient and cost effective production of high specificity probes.

Detection of specific sequences in a genome makes use of the fact that DNA consists of a helix of two DNA strands and that this double strand is most stable when these two strands are homologues. The DNA consists of a phosphate-sugar phosphate backbone and to every sugar one of four different nitrogenous bases, cytosine guanine thymine or adenine, might be present. Homologue strands pair every cytosine with a guanine and every thymine with an adenine. When a labeled homologue sequence is added to a genome and the DNA is made single stranded, these labeled sequences will hybridize, under the right circumstances, to the specific homologue sequence in tie genome. For this in situ hybridization, a number of probes are available for different detections purposes and applications.
Whole Chromosome/Paint Probes (WCP)

WCP incorporates labeled DNA material, homologous to a specific chromosome. The material is obtained by flow sorting of metaphase chromosomes or by laser dissection from a metaphase spread which is amplified by PCR or a related technique. After labeling and applying it to a properly prepared nucleus, it will stain the target chromosome. However, such labeled probes will in addition stain other non-target chromosomes because of structural or repetitive sequence elements that are shared among some or all chromosomes. Accordingly in order to stain only those sequences originating from the intended chromosome of interest, these common repetitive elements are usually inhibited by hybridization with blocking DNA or other methods that block or remove non-specific interactions.

Multiple chromosome paints are also applied to a single nucleus. WCP are labeled by different fluorochromes or with a combination of fluorochromes, providing no limit to the amount of WCP's applied in a single hybridization. WCP's axe mainly used for karyotyping and to study translocations of large fragments, regions and subregions of chromosomes which are best observed in a metaphase spread of a nucleus.

Centromere Probes

Centromere probes are targeted to a 171 bp sequence that occurs in repetitive order in every centromeric region of the human chromosomes. All chromosomes have a slightly different sequence and because of this all chromosomes are detected separately when the right hybridization stringency is used. Only two chromosome pairs, 13 with 21 and 14 with 22, share the same repeat and cannot be detected independently. Generally, centromeric probes are produced from plasmids containing an insert from one or a few copies of the 171 pb repeat. These probes are able to be hybridized without the addition of blocking DNA because the 171 bp sequences do not occur outside the regions of interest.

Telomere Probes

Human telomeres consist of an array of short repetitive sequences (i.e. TTAGGG). This is repeated several times in different amounts for every chromosome and individual test subject age. This repetitive sequence is used as a probe that will stain all chromosomes although not every chromosome will stain equally strong. To detect tie telomeric end of chromosomes, mostly a sub-telomeric bacterial artificial chromosome (BAC) clone is used. This BAC clone contains repetitive sequences which should be blocked or removed during or before hybridization.

Comparative Genomic Hybridization (CGH) Probes

CGH is a process that involves hybridizing a test genome to a reference genome. The reference genome may take the form of a metaphase chromosome spread from a healthy individual or may be array based using probe sequences that represent all or part of a genome. Microarray probes made using BAC clones contain repetitive sequences which must be blocked prior to hybridization. However; blocking has the potential to cause a deviation in the results when compared to repeat depleted probes (Knol and Rogan, Nucleic Acids Research, 2005, Vol. 33, No. 22). Further, the blocking step increases the cost of hybridization assays. If the probe sequences are depleted of repetitive sequences, the blocking step of the labeled genomic DNA is not necessary, resulting ill a reduction in the cost and removal of any variation.

Gene Specific Probes

Gene specific probes are designed to detect a region of the genome containing a target gene or group of genes. These probes are used to detect amplifications or deletions of specific genomic areas which correlated to the expression level of the specific gene of interest. The coding sequence of the gene(s) itself is not large enough to generate a detection signal for the probe that is visible using standard fluorescence microscope. Therefore such gene specific probes are not limited to just the coding gene sequences (exons) but also involve non-coding (introns), regulatory or other sequences around the gene. Because of the large sequences encompassed within even a gene specific probe design they often suffer from the undesirable inclusion of unwanted repetitive sequences. When such material is then either labeled and used in hybridizations or used in hybridizations and then labeled, the unwanted sequences must be blocked or removed from the probe to be able to detect the gene area specifically.

Microarray Probes

Similar to CGH, microarray probes are fixed to a carrier. In general, automated robotic techniques are used to spot cDNA-PCR products or synthetic oligonucleotides on a slide or similar fixed surface. Also, techniques exist to synthesize sequences directly on a slide (Affimetrix, Inc, Santa Clara).

The slides are hybridized with labeled cDNA or RNA in combination with different labeled cDNA or RNA as controls.

Coupling Reporter Molecules to DNA Probes

DNA probes are visualized by coupled reporter molecules. These molecules need to be incorporated in or attached to the DNA probe. One method utilizes a reporter molecule, having nucleotides linked to enzymatic reactions. Examples include incorporation by nick translation or a random prime reaction. Further, an amine coupled nucleotide, built in this way, is subsequently coupled directly or indirectly to reporter molecules. Coupling is done by chemical labeling of the DNA. An example is the coupling of a reporter molecule linked to a platinum group which forms a coordinative bond to the N7 position of guanine as used in ULS labeling (Kreatech Diagnostics, Amsterdam) and described in U.S. Pat. Nos. 5,580,990; 5,714,327; 5,985,566; 6,133,038; 6,248,531; 6,338,943; 6,406,850; and 6,797,818. Reporter molecules can be radioactive isotope, non-isotopic labels, digoxygenin, enzymes, biotin, avidin, streptavidin, luminescent agents such as radioluminescent, chemiluminescent, bioluminescent and photoluminescent, (including fluorescent and phosphorescent), dyes, haptens, and the like.

Sample Preparation

To be able to detect the labeled probes bound to interphase chromosomes, the nucleus should maintain morphology during and after the FISH procedures. Using fixation, cells or nuclei are attached to a solid layer such as a microscope slide. Fixation before during or after attachment to the solid layer, provide reference for identification. Depending on the type of cell or tissue, the nuclei have to be accessible for probe DNA, usually by pre-treating with proteolytic enzymes, heat, alcohols, denaturants, detergent solutions or a combination of treatments. Probe and nucleic DNA are made single stranded by heat or alkali treatment and then allowed to hybridize.

Use of DNA Probes

Microarrays

One common use of microarrays is to determine the RNA expression profile of a suspect tissue, tumor, or microbe. By analyzing the RNA expression profile, a prognosis for the treatment and survival of the patient is proposed. The prognostic value of RNA microarrays for clinical usage has yet to be determined. Another common use of microarrays are array based CGH. With this technique an entire genome can be screened for amplifications and/or deletions of chromosomal regions Microscopy Cytogenetic analysis in pre and post natal testing is used to determine whether or not a fetus has a cytogenetic abnormality in a cell population from the fetus. Samples are frequently obtained through aminocenthesis, conducted in pregnant women who are considered to have an increased risk for cytogenetic abnormalities. Accordingly, these cells are investigated for cytogenetic abnormalities. The same type of investigations are performed to confirm cytogenetic abnormalities or investigate suspect cytogenetic abnormalities in cell populations obtained after delivery.

Assessing Fetal Cells in Maternal Blood

During pregnancy, fetal cells may enter into the maternal blood with increases in the number of these fetal cells found with trauma, (pre)-ecclampsy and abnormal pregnancies. In routine assessments of fetomaternal hemmorrhages, the frequently used Kleihauer-Betke test is based on the detection of red blood cells expressing fetal hemoglobin. For detection of cytogenetic abnormalities, nucleated cells from maternal blood are needed. The frequency of these cells is considerably lower and are estimated to be in the range of 1-10 fetal cells per mL of maternal blood. Nucleated red blood cells, trophoblast cells and the presence of hematopoietic progenitors that are of fetal origin provide a target for isolation and probe hybridization in the detection of cytogenetic abnormalities early in the pregnancies. To date a reliable and reproducible method to identify and assess the cytogenetic composition of these cells is not available. One of the main problems with this analysis is the loss of fetal cells at various steps throughout the procedure, resulting in inconsistent or inconclusive information.

Oncology

FISH is used to detect various kinds of chromosomal aberrations like translocations, deletions, amplifications, inversions, and duplications. These aberrations are detected in all types of cells and tissue. In leukemia, cells are isolated from blood or bone marrow for subsequent FISH analysis. In bladder cancer, cells are isolated from urine. Cells from solid tumors are obtained by puncture or excision of the tumor itself. Also, cells that are released by solid tumors are isolated from the blood and analyzed by FISH. The latter gives the opportunity to monitor tumor treatment closely in order to detect a chromosomal change in the tumor. In some types of cancer, FISH provides a prognosis of tumor progression or predicts the efficacy of specific medication. Commercially, the most used FISH tests are the BCR-ABL translocation FISH in Chronic myelogenous leukemia and the her2/neu gene amplification FISH in breast cancer.

Disseminated Tumor Cells

Methods for the characterization of not only tumor cells, but also rare cells, or other biological entities from biological samples have been previously described (U.S. Pat. No. 6,365,362). This two stage method requires efficient enrichment to ensure acquisition of target cells while eliminating a substantial amount of debris and other interfering substances prior to analysis, allowing for cellular examination by imaging techniques. The method combines elements of immunomagnetic enrichment with multi-parameter flow cytometry, microscopy and immunuocytochemical analysis in a uniquely automated way. The combination method is used to enrich and enumerate epithelial cells in blood samples, thus providing a tool for measuring cancer.

The two stage method has applications in cancer prognosis and survival for patients with metastatic cancer (WO 04076643). Based on the presence of morphologically intact circulating cancer cells in blood, this method is able to correlate the presence of circulating cancer cells of metastatic breast cancer patients with time to disease progression and survival. More specifically, the presence of five (5) or more circulating tumor cells per 7.5 milliliters provides a predictive value at the first follow-up, thus providing an early prognostic indicator of patient survival.

The specificity of the assay described above increases with the number of cells detected and is not sufficient in cases were only few (generally less than 5 circulating tumor cells) are detected. One solution to this problem is to provide detailed genetic information about suspected cancer cells. Accordingly, a method that would incorporate enrichment of a blood sample with multi-parametric image cytometry and multi-parametric genetic analysis on an individual suspect cancer cell would provide a complete profile and confirmatory mechanism to significantly improve current procedures for patient screening, assessing recurrence of disease, or overall survival.

Fluorescent in situ hybridization (FISH) has been described as a single mode of analysis in rare cell detection after enrichment as described in WO 00/60119; Meng et al. PNAS 101 (25): 9393-9398 (2004); Fehm et al. Clin Can Res 8: 2073-2084 (2002) and incorporated by reference herein. After epithelial cell enrichment, captured cells are screened by known hybridization methods and imaged on a microscope slide. Because of inherent technical variations and a lack of satisfactory confirmation of the genetic information, the hybridization pattern alone does not provide a level of clinical confidence that would be necessary for sensitive analysis, as in assessing samples with less than 5 target cells. Further, this method for FISH analysis is difficult to automate.

Coupling hybridization-based methods with immunocytochemistry in the analysis of individual cells has been previously described (U.S. Pat. No. 6,524,798). Simultaneous phenotypic and genotypic assessment of individual cells requires that the phenotypic characteristics remain stable after in situ hybridization preparatory steps and are limited in the choice of detectable labels. Typically, conventional in situ hybridization assays require the following steps: (1) denaturation with heat or alkali; (2) an optional step to reduce non-specific binding; (3) hybridization of one or more nucleic acid probes to the target nucleic acid sequence; (4) removal of nucleic acid fragments not bound; and (5) detection of the hybridized probes. The reagents used to complete one or more of these steps (i.e. methanol wash) will alter antigen recognition in subsequent immunocytochemistry, cause small shifts in the position of target cells or completely removes the target cells, which introduces the possibility of mischaracterization of suspect cells.

Probe sets and methods for multi-parametric FISH analysis has been described in lung cancer (US 20030087248). A 3 probe combination resulting in 95% sensitivity for detecting bladder cancer in patients has also been described, see U.S. Pat. Nos. 6,376,188; 6,174,681. These methods lack the specificity and sensitivity for assessing small numbers of target cells, and thus a confirmatory assessment for early detection of disease state. They also do not provide a means for convenient automation.

One aspect of the present invention provides a confirmatory assay in the analysis of rare circulating cells by combining phenotypic and genotypic multiparametric analysis of an individually isolated target cell, resulting in a clinically significant level of sensitivity and, therefore, assurance to the clinician of any quantitative information acquired. Relevant disease states are assessed using extremely small (1, 2, 3, or 4) numbers of circulating tumor cells (CTC's) and provide a confirmation for early disease detection.

SUMMARY OF THE INVENTION

Generation of Repeat Depleted DNA Probes

One embodiment of the present invention includes methods and compositions to eliminate repetitive sequences from DNA. Any double stranded DNA is a suitable source in the application of the methods of the present invention. To obtain single stranded DNA, devoid of repetitive sequences, first an amplified whole genome library is made from the source DNA according to standard procedures. The library obtained consists of randomly selected fragments ranging in size from approximately 200 to 500 base pairs. Each fragment consists of double stranded DNA, having PCR primer sequences at each end of a target sequence. Generally, this library is representative of the source DNA. Other methods that results in modified fragments of DNA to permit amplification are also considered in this invention with no limit to the size of the fragments. These include, but are not limited to, degenerate oligonucleotide primed polymerase chain reaction (DOP PCR), rolling circles and isothermal amplification methods. Double stranded DNA fragments are denatured by heating up to 95° C. or other means to obtain single stranded DNA fragments. The resulting single stranded DNA fragments contain repetitive sequences, unique sequences or a combination of unique and repetitive sequences. An excess of Cot DNA or other appropriate subtractor DNA that binds to repetitive sequences is added. Subsequent lowering of the temperature results in the formation of double stranded DNA for only those fragments that contain repetitive sequences. Duplex Specific Nuclease (DSN) is added to allow digestion of double stranded DNA. In one embodiment, the DSN enzyme is added for 2 hours at 65° C. The resulting composition contains mostly single stranded DNA, having only unique sequences, and digested DNA. The unique sequence, now single stranded DNA with PCR primers at both ends, is used as a template to generate large amounts of the unique sequence for use in probe production. When BAC clones containing a desired unique sequence is used as source DNA, the template generated by this method contains only that unique sequence. When the boundary sequences are known, this method is useful in obtaining probes that cover the nucleotides between the boundary sequences in genomic DNA. Further, the present invention includes methods of use and compositions, resulting from the production of these DNA sequences after elimination of their repetitive sequences. These repeat depleted DNA sequences function as hybridization probes without the use of a blocking DNA in any appropriate application requiring disabling or blocking of undesired DNA sequences.

Another embodiment of the present invention provides for a system, apparatus, and methods in the preservation of immunomagnetically labeled cells for subsequent FISH analysis. This aspect permits the reanalysis of individual cells, utilizing the same or similar reporter molecules previously used to identify them. Accordingly after immunomagnetic selection and initial fluorescent labeling, the cells of interest are identified and their location is recorded. The cells are fixed in position followed by appropriate processing. Alternatively, the cells are fixed in position and stored for processing at a later point in time. For FISH applications, the sample is heated above the melting temperature of DNA, resulting in the loss of reporter molecules used to initially identify the target cells. After completing FISH in which the fluorescent FISH probes are hybridized and the nuclear material is again fluorescently labeled, the sample is reintroduced in an analyzer which locates the cells of interest to examine fluorescent signals from the FISH probes.

Another embodiment of die present invention provides methods for the reanalysis of immunomagnetically labeled cells as a confirmation in identifying rare circulating cells such as circulating tumor cells (CTC's). Thus, methods and techniques for the further processing of cells after enrichment, immunofluorescent labeling and subsequent confirmatory analysis, using in situ hybridization, as a means to increase specificity and thereby confirm the identity of suspect CTC's in patients as being cancer cells. Cytogenetic abnormalities detected in morphologically suspect CTC's, detected in metastatic carcinoma patients, have a prognosis similar to patients with morphologically obvious CTCs or having an abundance of CTCs. One embodiment of the present invention considers confirmation assays in patients diagnosed with carcinomas and having CTCs, or disseminated tumor cells (DTC's) in bone marrow, where there is an increased risk for recurrence. In addition, the methods of the present invention are applicable when there is a need to assess for the presence or absence of drug targets in CTC such as, but not limited to, Her1, Her2, Androgen Receptor (AR), cMyc, or P10.

DETAILED DESCRIPTION OF THE INVENTION

Generation of Repeat Depleted DNA Probes

DNA contains unique as well as repetitive sequences. The repetitive sequences occur throughout the chromosomes and have the potential to interfere with hybridization reactions, such as with in situ hybridization, targeted toward specific regions or unique sequences outside these repetitive sequences. To identify the presence, amount and location of specific sequences on chromosomes, genes or DNA sequences it is important that the hybridization probes hybridize only at the location of interest. The presence of repetitive sequences in the hybridization probe mixture reduces the specificity of the binding, requiring methods to either remove the repetitive sequences from the probes or prevent the probes from hybridizing to the repetitive sequences on the target. For example, Cot-1 DNA is often added during hybridization to prevent binding of the probes to the repetitive sequences (U.S. Pat. Nos. 5,447,841 and 6,596,479).

Recent contributions have addressed this question by disabling the repetitive sequences. The use of Cot-1 DNA relies on the ability of Cot-1 DNA to form a duplex structure with available single strand repeat sequences, and thereby minimize non-specific binding interaction of this portion of the sequence with the unique target sequence. Blocking the repetitive DNA, either during a hybridization step with the unique target sequence or prior as in a pre-association step, results in a mixture having repetitive segments forming duplex structures with their complementary sequence aid a single strand form of the target probe, available for hybridization to its unique target segment. Unfortunately, the presence of this duplex in a subsequent amplification or labeling reaction affects the signal through the introduction of non-specific noise, especially in situations where the signal is very weak. An alternative to blocking the repetitive sequence is to remove the unwanted repeat segments from the reaction mix.

Figure 1:
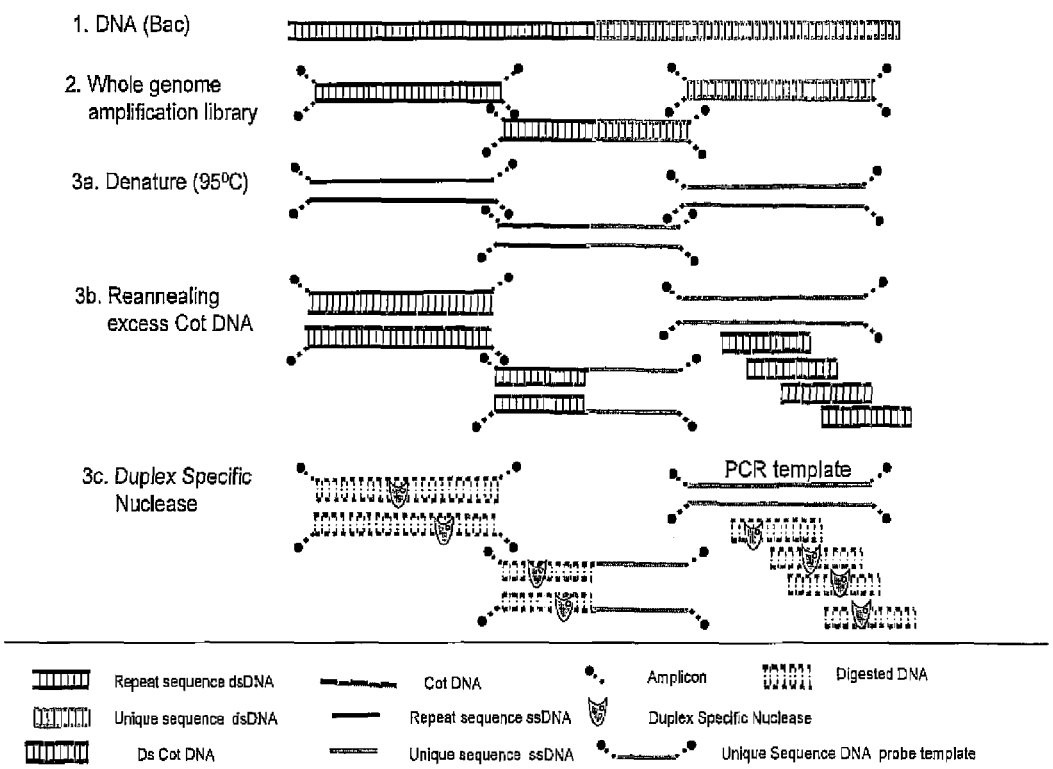
FIG. 1: Schematic representation depicting the generation of repeat depleted DNA probes from BAC starting DNA. A fragmented whole genome amplification library is denatured and allowed to re-anneal in the presence of excess Cot DNA. DSN digestion of the double strand DNA results in a mixture of single strand unique sequence, available as a template for probe production.

Generation of repeat-depleted DNA probes of this prevention is depicted in FIG. 1. One embodiment of the present invention makes use of duplex specific nucleases (DSN) which preferentially cleave deoxyribonucleic acid molecules (US 2005/0164216 and U.S. Pat. No. 6,541,204 incorporated by reference). The ability of the enzyme to preferentially cleave nucleic acid duplex polynucleotides as compared to single strand DNA provides a means for removing non-target double stranded DNA from the sample mixture. The ability of these nucleases to preferentially digest the duplex form of polynucleotides provides potential use in manufacturing an unique target specific probe, eliminating the interfering affect of blocking DNA, and providing a means for their rapid, efficient and cost effective production.

Starting DNA used in the practice of this invention is typically in the form of one or more DNA sequences which contain a multiplicity of DNA segments. The initial source of individual starting material in the production of the probe composition has been described in the production of direct-labeled probes (U.S. Pat. No. 6,569,626). Optimally the source of the starting polynucleotide is purified from tissue and fragmented into 150 kb to 200 kb segments, using any known technique such as, but not limited to, enzyme treatment (restriction enzymes), polymerase, limited DNase I digestion, limited mung bean nuclease digestion, sonication, shearing of DNA, and the like. Some of these segmental fragments will be complementary to at least a portion of one or more DNA segments in the particular unique target sequence. The individual DNA segments are propagated by commonly known methods, such as cloning into a plasmid construct and then transfected into bacteria. After propagating the cloned fragments, individual colonies representing isolated fragments are identified as containing at least a portion of the sequence of interest. Identification is accomplished by known techniques such as hybridization, PCR, or searching established databases of commercially available libraries. Each chosen colony is grown to obtain an isolated plasmid construct having a unique fragment, at least partially complementary to a segment of the target sequence on the chromosome. Exemplary target sequences include HER-2, IGF-1, MUC-1, EGFR, and AR and may be available through commercial vendors (i.e. BAC clones). Once the cloned fragments of interest are propagated and isolated, they are depleted of their repetitive polynucleotide sequences. Using whole gene amplification (WGA), the fragments are amplified as 200 to 500 bp segments from the isolated plasmid constructs. Commercially available DOP PCR is considered as one embodiment to this portion of the procedure. Cot-1 DNA is combined with the WGA library pool after amplification by first heating to 95° C. to denature the double-strand polynucleotide into a single strand state and then cooling to 65° C. to allow selective re-annealing of the repeat sequences. Duplex specific nucleases (DSN) under optimized DSN conditions are then added to preferentially cleave deoxyribonucleic acid molecules containing perfectly matched nucleic acid duplexes while not affecting any remaining single stranded segments. Selectively cleaving the duplex nucleic acids is accomplished by enzymatic digestion of DNA-DNA duplexes and DNA-RNA duplexes. Specific embodiments of the present invention include DSN isolated from the Kamchatka crab (U.S. Ser. No. 10/845,366) or shrimp (U.S. Pat. No. 6,541,204), but any enzymatic removal of duplex structure is considered in the present invention. The use of endo-nuclease-specific nucleases hydrolyzes a phosphodiester bond in the duplex DNA backbone, providing the advantage of not being nucleotide sequence-specific and therefore applicable to most targets of interest. DSN digestion provides for the removal of a substantial amount of the nucleic acid duplex for subsequent amplification of the remaining single-strand polynucleotide. One embodiment of the present invention is a 2 hour DSN digestion at 65° C. The resulting composition contains single stranded DNA, corresponding to portions of the unique target sequence on the chromosome, some amount of undigested double-strand DNA, and digested base pairs. Preferably, the undigested DNA is separated from the digested DNA and the DSN by centrifugation (i.e. spin column chromatography). The mixture is used immediately or stored at 80° C., either before or after amplification of the purified composition for subsequent utilization such as labeling and use for in situ hybridization. After amplification, the resulting target probe sequence is amplified by PCR yielding 90% to 99% pure target probe sequence, and designated repeat-depleted DNA.

The use of DSN in the enrichment and isolation of a single strand polynucleotide from double strand is applicable in the production of any single strand polynucleotide wherein separation of the single strand entity from double strand contaminants is desirable. This is particularly relevant, although not limited, in the production of labeled probes for gene or chromosome identification, karyotype or panning a pool of single strand mid double strand polynucleotides.

The resulting probes, both composition and production, are incorporated in the subject matter embodied in the present invention. Repeat-depleted DNA, as described in the present invention, is useful for in situ hybridization, including FISH, and all other nucleic acid hybridization assays. The requirement for competitive binding is eliminated using the repeat-depleted probes described in this invention, resulting in increased specificity of the reaction and a reduction in the amount of probes necessary for binding.

The Duplex Specific Nuclease Method

To make a hybridization probe toward a target sequence, DNA containing the sequence of interest is obtained. Methods to obtain DNA containing sequences of interest will be known to those skilled in the art and include, without limitation, isolation of genomic DNA from tissues or cells, flow sorting of chromosomes, and screening libraries of cloned fragments of chromosomes by hybridization, electronically, or PCR.

Starting DNA used in the practice of this invention is purified from a source by any method. Typically the starting DNA consists of genomes, chromosomes, portions of chromosomes, or cloned fragments of chromosomes. Flow—sorted chromosomes and Bacterial Artificial Chromosomes (BAC) known to contain target sequences of cancer related genes make the present invention particularly applicable. Exemplary target sequences include HER-2, IGF-1, MYC, EGFR, and AR. BAC clones containing these sequences are available through commercial vendors.

Once the DNA containing sequences of interest are identified and obtained, they are depleted of repetitive polynucleotide sequences. This process begins by fragmenting and preparing a library containing the sequence of interest. One method is the GenomePlex® Whole Genome Amplification (WGA) method (GenomePlex® is a trademark of Rubicon Genomics, Inc.) that randomly cleaves the cloned fragments into 200-500 bp fragments and attaches linker sequences which can then be used to amplify and re-amplify the library using PCR. In this example the fragmented, amplified library is considered the source DNA.

To remove the repetitive sequences, the source DNA is denatured to a single stranded state and then cooled under conditions that selectively allow repetitive sequences to anneal to form double stranded molecules and unique sequences to remain single stranded. A duplex specific nuclease (DSN) is then added which preferentially cleaves the double stranded repetitive fragments while not cleaving the single stranded unique sequences. The resulting mixture contains single stranded DNA, corresponding to portions of the unique target sequence on the chromosome, some amount of undigested double-strand DNA, and digested base pairs. Preferably, the undigested DNA is separated from the digested DNA and the DSN by spin column chromatography, phenol chloroform extraction or some other similar method, but separation is not a requirement. Then, the repeat-depleted library is used as a hybridization probe or re-amplified using PCR to prepare larger amounts of probe DNA. After amplification, the resulting target probe sequence is 90% to 99% pure target probe sequence, and designated Repeat-depleted DNA.

The library fragmentation and amplification methods described above are not intended to be limiting but rather serve as an example of how one fragmentation and amplification method is used to make repeat-depleted probes. There are numerous methods of fragmenting and amplifying nucleic acids including linker-adapter PCR, DOP PCR, rolling circle amplification, transcription-mediated amplification and all other methods are considered this invention. It is expected that some modification of the above method to prepare repeat-depleted DNA will be necessary to accommodate the different methods of library fragmentation and amplification and these modifications are also included in the present invention.

One consideration in this invention is the use of an enzyme that is capable of cleaving double stranded DNA while not cleaving single stranded DNA. Enzymes included in this invention may cleave double stranded DNA in any way, including lysis of the sugar-phosphate backbone, removal of one or both strands hi a DNA duplex or removal of nitrogenous bases to form apurinic/apyrimidinic sites. Non-limiting examples of these enzymes include endonucleases, exonucleases, restriction enzymes, nicking enzymes, DNA repair enzymes, topoisomerases, DNA gyrases, and enzymes involved in homologous recombination. Specific embodiments of the present invention include DSN isolated from the Kamchatka crab (U.S. Ser. No. 10/845,366), shrimp (U.S. Pat. No. 6,541,204), T7 Endonuclease I, and E. coli exonuclease III, all incorporated by reference.

Enzyme concentration, time of digestion, and buffer conditions such as salt and magnesium ion concentration are factors that can affect the specificity of DSN toward double stranded DNA. Optimization of these conditions is necessary to get efficient repeat-depletion.

Efficiency and specificity of repeat removal in this invention are dependent on the reaction conditions used to denature and re-anneal as well as the conditions present during digestion with the DSN. Denaturation is accomplished by alkali or heating. The degree of DNA re-annealing is dependent on the concentration of DNA present in the samples and the time allowed for re-annealing. In order for selective re-annealing of repetitive sequences to occur, the repeat sequences must be present in a higher concentration than the unique sequences. The ratio of repeat to unique sequences within a particular clone will vary from region to region throughout the genome. To standardize the depletion process across regions with varying numbers of repeat sequences, an excess of subtractor DNA is added to the reaction. The mass of subtractor DNA added varies depending on the desired amount of repeat removal and is preferably 10-50 times the mass of the source DNA. The present invention considers that a subtractor is any nucleic acid or nucleic acid analogue containing sequences sufficiently homologous in nucleotide sequence to the repetitive sequences as to allow hybridization between subtractor sequences and a portion of the sequences in the source DNA, making the subtractor sequence useful. One embodiment of the present invention includes Cot-1 DNA as a subtractor DNA which is used to remove repetitive sequences from source DNA.

The stringency for re-annealing is another component in the present invention. Salt concentration and temperature are factors that determine the stringency of any re-annealing step. The degree of repeat removal is controlled by adjusting stringency conditions for this step. Adjusting the stringency conditions to allow some degree of annealing between sequences that are not 100% homologous improves the degree of repeat removal. Salt concentrations range from 5 millimolar to 1000 millimolar NaCl with annealing temperatures range from 15° C. to 80° C.

In one embodiment, the repeat-depletion process is performed such that re-annealing and DSN digestion occur sequentially. Accordingly, the DNA is denatured and allowed to cool for a period of time under conditions optimized for annealing. Then, the reaction conditions are changed to conditions that optimize the specificity and activity of DSN digestion. In another embodiment the re-annealing and DSN digestion take place simultaneously, under the same conditions.

Also within the scope of this invention, the source or subtractor DNA is treated with an agent, either chemical or physical, before or during enzymatic digestion to alter the specificity of an enzyme toward either the single stranded or double stranded fractions within the mixture. For example, *E. coli* RecA protein is added to a mixture of single stranded and double stranded DNA. This protein coats the single stranded DNA in the mix and protects the single strand DNA from *E. coli* RecBC DNase while allowing the double stranded DNA in the mixture to be digested (*"Escherichia coli* RecA protein protects singles stranded DNA or Gapped Duplex DNA from degradation by RecBC DNase". Williams, J G K, Shibata, T. Radding, C M Journal of Biological Chemistry V246 no. 14 pp 7573-7582). It is also possible to generate source or subtractor DNA using modified nucleotides which alter the specificity of an enzyme toward the single strand or double strand DNA fractions.

The use of DSN hi the enrichment and isolation of a single strand polynucleotide from double strand is applicable in the production of any single strand polynucleotide wherein separation of the single strand entity from double strand contaminants is desirable. This includes removal of any undesirable sequence from a source DNA. These undesirable sequences include without limitation, repetitive sequences, unique sequences, and vector sequences. This method is particularly relevant in the production of labeled probes for gene or chromosome identification, karyotyping, or panning a pool of single strand and double strand polynucleotides.

The Selective Binding Method

By denaturing source DNA and selectively allowing repetitive sequences to anneal, any agent that binds preferentially to a single or double stranded DNA structure is used to remove repeat sequences from source DNA. Examples of these agents include, without limitation, DNA or RNA polynucleotides, enzymes, antibodies, DNA binding proteins, combinations of antibodies and DNA binding agents, and natural or synthetic compounds and molecules. DNA binding agents may be linked directly or indirectly to a solid support which allows for positive or negative chromatographic selection of unique or repetitive sequences. One example includes separation of single and double strand DNA using biotinylated antibodies toward single strand or double strand DNA. The desired population is separated using streptavidin-coated paramagnetic particles. Alternately, a biotinylated antibody toward a DNA binding agent that preferentially binds single or double strand DNA is used in the same fashion.

Other Single or Double Strand Specific Enzymes

The present invention also embodies any enzyme that preferentially acts on single or double strand DNA in modifying source or subtractor DNA in facilitating repeat removal. One non-limiting example is to selectively ligate a DNA linker to the double stranded DNA population after denaturation and selective re-annealing the repeats. This linker is hybridized to a homologous oligonucleotide attached to a magnetic (or paramagnetic) particle to remove repetitive sequences. A second example is to use a single strand DNA/RNA ligase to selectively circularize single stranded DNA present after denaturation and selective re-annealing the source DNA. The resulting circles are then be amplified and enriched by rolling circle amplification.

Structure Specific Separation of Repetitive Sequences

In addition to specific probe production methods and based on separation of single stranded DNA from double strand DNA, the present invention considers any method known in the art whereby separation of repeat sequences from unique sequences occurs with the establishment some detectable DNA structure in either the repeat sequences or the unique sequences and this detectable structure is used to separate one population from the other. Some examples of detectable DNA structures include without limitation, triple or quadruple stranded DNA, hairpins, panhandles, flaps, Z-DNA, Holliday junctions and other structures formed during recombination. These structures may be naturally occurring within the sequences of interest or they may be induced by modifying either or both the source nucleic acid or the subtractor nucleic acid.

Selective Digestion of Repeat Sequences

Another method to remove repeat sequences from source DNA is to digest a fragmented and amplifiable DNA library with a restriction enzyme whose recognition sequence is known to exist only in repetitive DNA sequences. When the digested source DNA is re-amplified by PCR, the remaining library will be enriched for unique sequences and depleted of sequences that contain repeats.

Digestion and Selective Ligation

Another method is to prepare repeat-depleted probes is to digest target DNA with two restriction enzymes that leave different overhangs on the digested sequence. The first restriction enzyme is preferably an enzyme that cuts within the repeat sequences and the second is an enzyme that the does not cut within the repeat sequences. Following digestion, linkers are selectively attached to the ends of the sequences cut by the second restriction enzyme. These linker sequences are then used to PCR amplify a library, depleted of repeat sequences. The resulting repeat-depleted DNA, both composition and production, are incorporated in the present invention. Repeat-depleted DNA, as described in the present invention, is useful as probes for any type of hybridization assay where specific binding of target sequences is desired. These techniques include, without limitation, ISH, FISH, CGH spectral karyotyping, chromosome painting, Southern blot, Northern blot, and microarrays. Production of hybridization probes that only contain unique sequence is one embodiment of the present invention. Consequently, the requirement for competitive binding is eliminated, resulting in an increase in the specificity of the reaction, and reducing the amount of probes necessary for binding.

Use of Duplex Specific Nuclease to Cleave DNA at a Desired Location.

Figure 2:
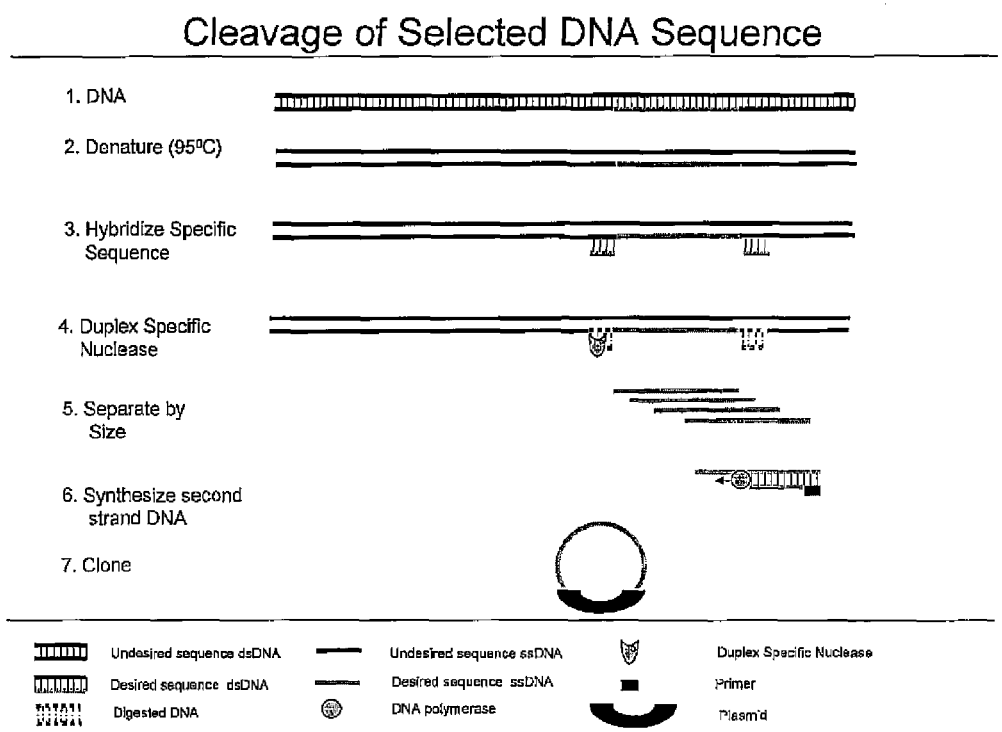
FIG. 2: Schematic representation depicting the cleavage of a specific DNA sequence from a DNA source and production of clones thereof. Double stranded DNA from an appropriate source is denatured and specific DNA sequence is allowed to hybridize. DSN digestion of the double strand DNA followed by separation of single strand DNA by size results in isolation of the desired single strand DNA. After synthesis of the second strand, the desired DNA is cloned into an appropriate vector for production.

The use of duplex specific nucleases has utility in cleaving specific sequences from DNA. avoiding the use of BAC clones, and increasing the specificity of the DNA probes. FIG. 2 show a schematic representation of this embodiment. Single strand DNA is obtained from a DNA source, containing the desired sequence. Primers identifying both ends of the desired sequence are added, and duplex specific nucleases introduced to cut the desired DNA probe from the source DNA. After separating the desired DNA probe by size exclusion, second strand DNA is synthesized and cloned to provide a source for DNA probes. Thus, duplex specific nuclease are used to cleave DNA sequences at specific regions. This method is most useful in isolation of fragments of interest when the fragments lack appropriate restriction enzyme sites. In FIG. 2, two oligonucleotides are designed to anneal to one or both strands of the DNA, and flank the sequence of interest. DNA containing a sequence of interest is denatured and allowed to re-anneal in the presence of an excess of the flanking oligonucleotides. Digestion with a duplex specific nuclease selectively cuts the DNA at tie site where the oligonucleotides are annealed. The remaining single strand DNA molecules are fractionated by size to obtain the sequence of interest. The sequence of interest is made double stranded using a DNA polymerase and cloned into a plasmid. Thus making possibilities to clone or subclone sequences of interest from a larger DNA polynucleotides. A second example of site specific cleavage is the recovery of cloned fragments from plasmid vectors by selectively digesting the vectors. In one example, the plasmid containing cloned DNA fragment is denatured and allowed to re-anneal in the presence of excess plasmid, lacking cloned DNA. Addition of a duplex specific nuclease cleaves the plasmid sequences and leaves the single strand cloned DNA intact. The remaining single strand DNA is then be used for any application known in the art including, but not limited to, sequencing or subcloninig.

EXAMPLE 1

Detection of Chromosomes or Portions of Chromosomes Using Repeat-Depleted DNA Probes BAC clone CTD-2019C10 was selected to be used as a probe for the Her-2 gene by electronically screening the human genome using the UCSC Genome Browser software (http://genome.ucsc.edu/cgi-bin/hgGateway) and clones were obtained from Invitrogen (Carlsbad, Calif.). BAC DNA was isolated using the Large Construct Kit from Qiagen (Valencia, Calif.). Source DNA was prepared using 10 nanograms of purified BAC and the Genomeplex® Complete Whole Genome Amplification Kit (Sigma-Aldrich St. Louis, Mo.) according to the manufacturer's directions. Depletion mixes were prepared containing 2 micrograms of Cot-1 DNA, 1×Duplex Specific Nuclease buffer (Evrogen, Moscow, Russia), 0.3 molar NaCl, and 66 nanograms of source DNA. The depletion mixes were denatured for 5 minutes at 95° C., placed on ice for 10 seconds aid 1 unit of Duplex Specific Nuclease (Evrogen, Moscow, Russia) added. Samples were incubated at 65° C. for 90 minutes. Five microliters of the reaction were purified using the Genelute PCR Clean-Up Kit (Sigma-Aldrich St. Louis, Mo.) and the purified DNA was eluted in 50 microliter aliquots. Fifteen microliters of the depleted samples were then re-amplified by PCR using the Whole Genome Re-amplification kit (Sigma-Aldrich St Louis, Mo.). PCR reactions were purified as described and quantified based upon their $A_{260}$. Ten nanograms of the first re-amplification mixture was used as template in a second re-amplification, purified as described. This material was sonicated to an average molecular weight of 200-500 base pairs, ethanol precipitated, and resuspended in distilled $H_2O$. The resulting DNA was fluorescently labeled using the Kreatech ULS Platinum Bright Red/Orange Kit (Kreatech, Amsterdam, Netherlands). For comparison, probes with repeats were also made from the source DNA which was used in the depletion process.

Figure 3:
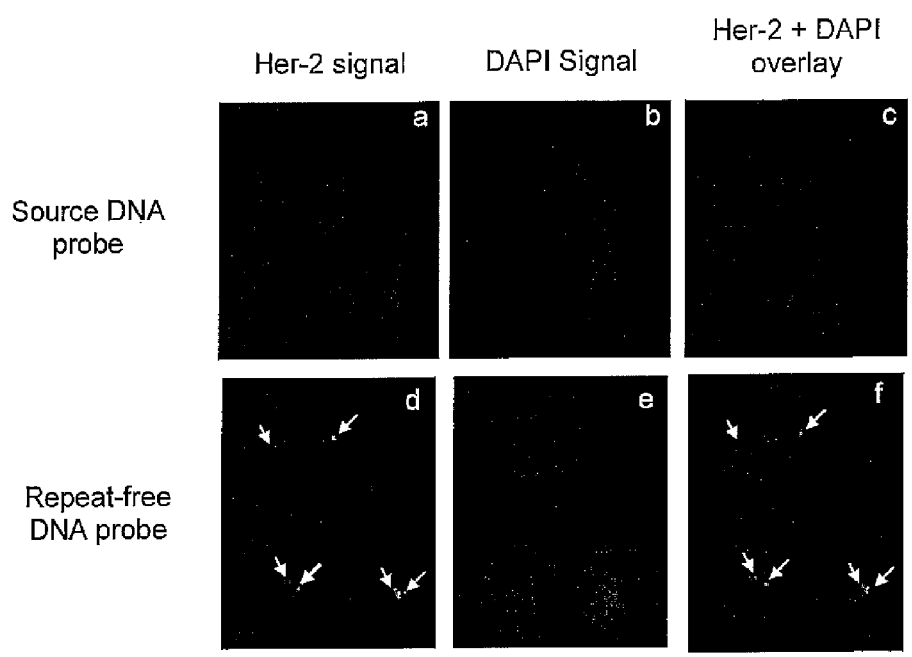
FIG. 3: Comparison using repeat-depleted probes in FISH analysis. White blood cells hybridized with a Her-2 probe containing repeats and no blocking DNA. In the absence of blocking DNA, the probe labels the entire nucleus after hybridization with repeat regions. Panel A shows white blood cells hybridized with a Her-2 FISH probe containing repeats and no blocking DNA. Panel B shows the sane cells after labeling the nucleus with DAPI. Panel C shows the overlay of the two signals and the lack of Her-2 resolution. Panel D shows FISH analysis on white blood cells using repeat-depleted a Her-2 probe. Arrows indicate locations of unique chromosome sequence for Her-2. Panel E shows the same cells after labeling the nucleus with DAPI. Panel F shows the overlay of panel D and B, visualizing the location of the Her-2 site within the cell nucleus.

Phytohemagglutimin-stimulated white blood cells were prepared for FISH by fixation in 75% methanol, 25% acetic acid and spotted on slides using standard techniques. Repeat-depleted probes and source DNA probes were hybridized at 2 ng/μl without Cot blocking DNA in a hybridization buffer consisting of 50% formamide, 10% dextran sulfate, and 1×SSC. Slides and probe were co-denatured at 80° C. for 3 minutes and hybridized overnight at 37° C. Following hybridization, samples were washed for five minutes at 50° C. In 0.5×SSC, 0.001% SDS. Samples were counterstained in 0.5 μg/ml DAPI for 5 minutes and mounted in 50% glycerol. Images were acquired using a Leica DM-RXA fluorescent microscope (Leica Microsystems, Bannockburn, Ill.) equipped with filters appropriate for rhodamine and DAPI. Images were acquired with a Photometrics SynSys black and white digital camera (Photometrics, Tucson, Ariz.). DAPI signals were enhanced and overlay images were generated using Leica FW 4000 software. Her-2 images are unedited and were captured using identical camera settings comparison purposes. FIG. 3 depicts a comparison of the images. Panel A shows that when source DNA containing repeats is used as a hybridization probe, the probes stain the entire nucleus and no Her-2 specific signals are visible. When repeat-depleted DNA is used as a probe (Panel D) specific signals that correspond to the Her-2 gene are clearly detectable (arrows).

EXAMPLE 2

Figure 4:
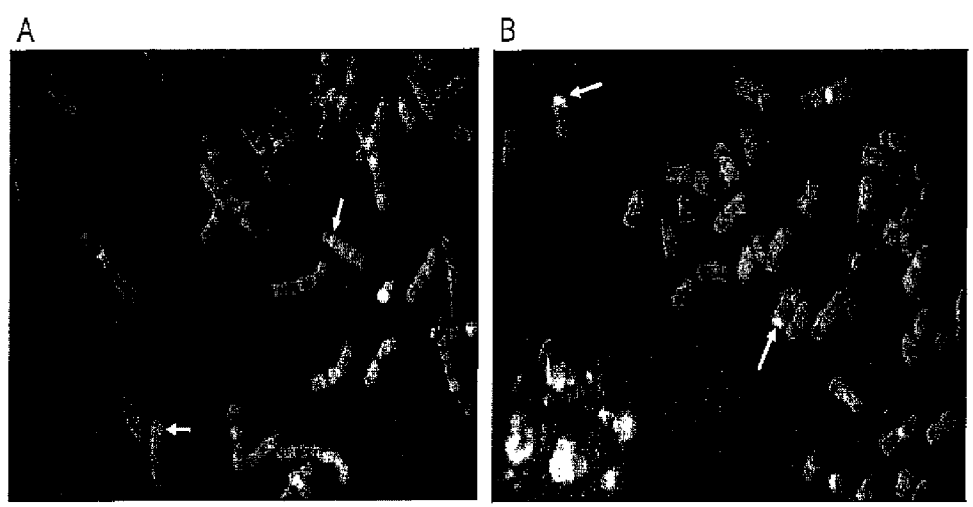
FIG. 4: Panel A shows a chromosome spread hybridized with a P16 (CDKN2A) labeled repeat free probe targeting 9p21 frequently used to characterize melanoma. Two chromosomes show the presence of 9p21 and are illustrated by arrows. Panel B shows a chromosome spread hybridized with MLL labeled repeat free probe targeting 11q23 used to identify a specific type of leukemia. Two chromosomes show the presence of 11q23 as illustrated by arrows.

DNA Probes Depleted from Repeat Sequences According to this Invention Improves the Visualization of Fluorescently Labeled DNA Probes as Compared to Traditional DNA Probes that Contain Repeats which are Blocked During the Procedure The signal to noise ration of fluorescently labeled probes is significantly improved when employing repeat depleted DNA probes obtained according to the invention. For this comparison, DNA probes targeting 9p21 and 11q23 were used as they are known to those skilled in the art. These signals are problematic in that they are relatively small signals and difficult to discern. Probes were depleted from repeat sequences according to the invention and fluorescent reporter molecule linked to a platinum group which forms a coordinative bond t the N7 position of guanine was used to fluorescently label the probes (ULS labeling, Kreatech, Amsterdam). FIG. 4 Panels A and B show a chromosome spread hybridized with rhodamine labeled 9p21 and dGreen labeled 11q23 probe respectively. Clear signals from the repeat free probes can be discerned with the repeat free probes as indicated by arrows in the figures. Thus, the visualization of the presence of these probes is superior to those that are obtained using probes that are obtained through traditional methods. This improvement in visualization provides a more accurate differential diagnosis of melanoma (Panel A, 9p21, P16 (CDKN2A) and leukemia (Panel B, 11q23, MLL).

Preservation of Immunomagnetically-Labeled Cells for Subsequent Analysis

During immunocytochemistry (ICC) image analysis the cells are magnetically held to the optically transparent surface of the cartridge by magnetic forces applied by an external magnet (U.S. Pat. No. 5,466,574). The calculated holding force of the device is approximately $10^{-9}$ Newtons. This holding force is dependent upon several variables including but not limited to the number of ferrofluid particles on the cell, the size of the magnetic particles and the magnetic field gradient applied by the external magnet. ID order to fix the cells to the glass surface, the buffer solution must be removed and replaced by a cell fixative solution, such as methanol, acetone, acetic acid, other agents known in die art and combinations of these. Aspiration of the buffer solution must be carefully completed so as to not displace or remove the cells to be analyzed. So as fluid is aspirated from the sample chamber, the meniscus of the fluid applies shear forces on the magnetically held cells. These shear forces can be greater than the magnetic holding forces (calculated at greater than $10^{-9}$ Newtons). In such situations, the cells will either be moved within the cartridge or displaced such that they are aspirated from the cartridge along with the buffer solution. Fluid shear forces are a function of the rate at which the meniscus moves across the glass portion of the cartridge, the distance between the aspiration probe and the glass surface, the velocity and viscosity of the fluid being aspirated and other parameters. Additionally after aspiration, any drying of the glass surface before the fixation solution is added can have a negative effect on the cells within the cartridge. Plus, the addition of a fixation solution into an empty cartridge will further disturb the distribution of the cells.

Accordingly, one aspect of the present invention address these issues by providing a method for replacing the buffer solution with the fixation fluid without subjecting the cells to fluid shear forces caused by the meniscus. Fixation solution is dispensed into the bottom of the cartridge with the simultaneous aspiration of the displaced buffer solution from the top of the cartridge. While some mixing of fixative and buffer will take place at the interface of the two fluids, sufficient fixation solution will be dispensed to complete the required cell fixation to the glass surface. This fluid displacement will occur with minimal shear forces applied to the cells in the cartridge by balancing the flow between the dispensed fixative solution and aspiration of the displaced fluid, in addition to the magnetic holding force retaining the immunomagnetic attached cells to the surface of the glass. One preferred embodiment of the present invention utilizes the entry area of sample chambers described in U.S. Pat. No. 6,861,259; U.S. Ser. No. 10/988,057; and U.S. Pat. No. 7,011,794; U.S. Ser. No. 11/294,012 in displacing approximately 100 microliters of fluid within the cartridge without spilling out of the cartridge. The opening port of the cartridge is sufficient to allow an aspiration probe to remove buffer solution as the fixative solution is being dispensed to displace the buffer solution. Once the cells have been fixed in place by the fixation fluid, the fluid may be removed without risk of cell disturbance. This procedure allows for automated processing of samples for subsequent FISH or other analysis with minimal operator interaction that could introduce variability into the preparation process.

Figure 5:
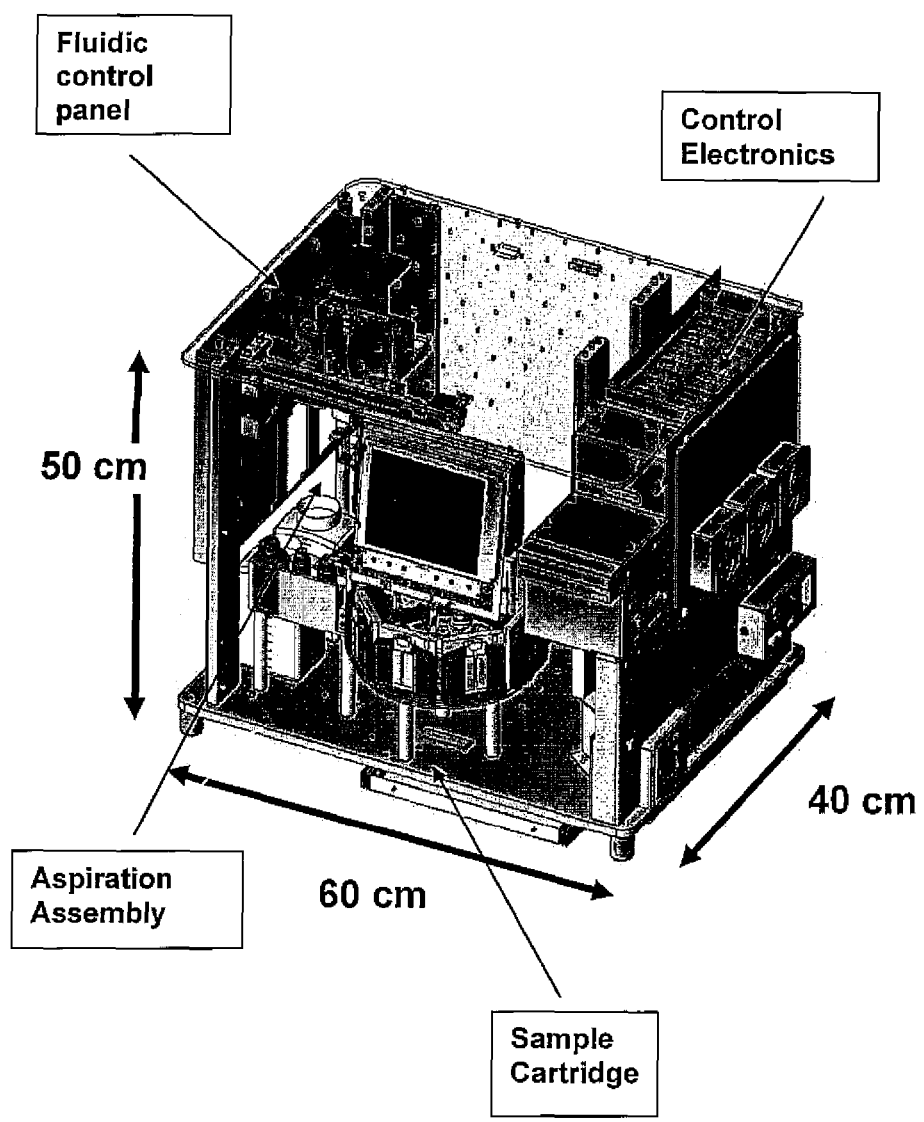
FIG. 5: Schematic representation of the fixation and hybridization device used to prepare samples for FISH analysis. A compact and portable device for preparing a sample for FISH analysis after immunomagnetic enrichment and initial fluorescent imaging. Shown are the control panel, electronics, pump, and poser supply in relation to the sample cartridge.
Figure 6:
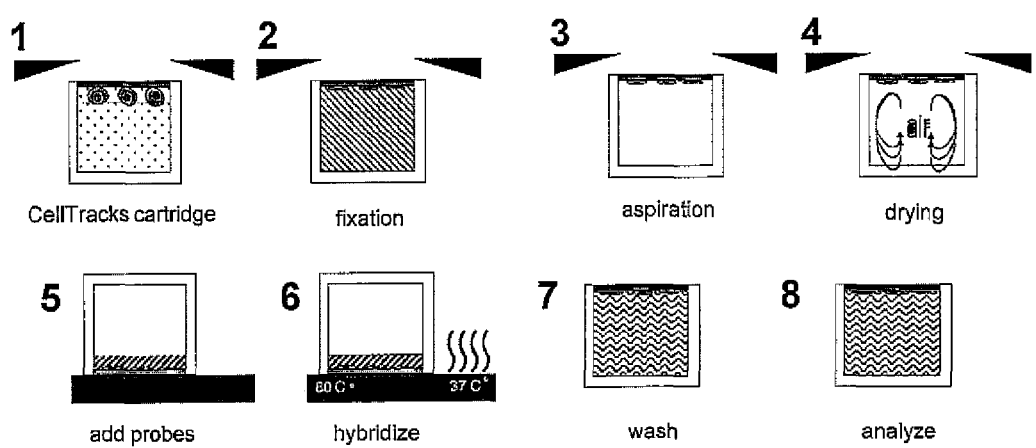
FIG. 6: Schematic representation of the basic steps for FISH after initial fluorescent imaging. Shown are cross-sectional images of the sample cartridge and the presence of magnetic support (black wedges). Panel 1 shows the cells arranged along the internal surface of the imaging face of the cartridge after initial fluorescent imaging using CellTracks System. Panel 2 shows the simultaneous replacement of the buffer solution with a fixative for FISH. In Panel 3, the fixative is aspirated to remove fluids from the cartridge. Panel 4 shows the addition of forced air to dry the cartridge. In Panel 5, the cartridge is inverted and enough FISH probe is added to cover the cells. Panel 6 shows the cartridge on a heat source to allow hybridization. In Panel 7, the FISH reagents are washed to allow rescanning and analysis of the FISH signals in Panel 8.

The present invention describes an automated device which allows for complete and consistent fixation of cells in the cartridge after ICC imaging in a bench-top device, and incorporates all the steps in the preparation of target cells after ICC for subsequent FISH image analysis. FIG. 5 depicts a schematic view of the apparatus showing the relative locations of the individual components. Accordingly, the cartridge containing the ICC imaged sample is placed into the device for buffer removal and fixation. A syringe and syringe pump in combination with a pipette aspirates the buffer and dispenses the fixative. FIG. 6 is a schematic representation of the steps involved in the fixation and hybridization of the cells. In one embodiment of the invention the buffer removal and addition of fixative are performed simultaneously to minimize cell movement through the forces exhibited by the fluid removal and addition. The fixation is completed by removal of all fluids from the cartridge followed by drying of the cartridge by a forced air flow inside the cartridge using the same pipette as used for the addition and removal of fixation reagents. After fixation and drying the cartridge is stored or used immediately for FISH or other additional analysis. Optimal mixtures for the fixative differ depending on the target entity (i.e. DNA, RNA, protein).

Fixation Protocol for FISH

To fix the cells on the upper surface and leave them intact and accessible for FISH probes, the following protocol is developed and implemented in the automated bench-top device:
1. Dispense 250 microliters of fixative from tie bottom of the cartridge (cartridge in up-right position).
2. Aspirate 250 microliters from the top and dispose.
3. Repeat the dispense 250 microliters new fixative from the bottom of the cartridge.
4. Aspirate all fluid from the top of the cartridge.
5. Dry the cartridge by flowing air through the cartridge. Pipette used for aspiration/dispensing is used for air flow as well.

Volume Reduction

As a consequence of the expense of antibodies or polynucleotide probes and the requirement to use them in high concentrations, reactions are carried out in very small closed volumes (for example 5 microliters to 25 microliters) so the cost of using a high concentration is offset by having to use very small volumes of reagents. Sample cartridges as described in U.S. Pat. No. 6,861,259; U.S. Ser. No. 10/988,057; and U.S. Pat. No. 7,011,794; U.S. Ser. No. 11/294,012 are used as the reaction vessel after immobilization in the chamber. In these cartridges, the immediate volume of the chamber where the cells are immobilized is 320 microliters. Thus, there is a need to analyze immobilized cells by in situ hybridization, but the adding 320 microliters of a high concentration of most probes are expensive and impractical.

To address this problem, a uniform distribution of the probe mixture across the surface of the optically transparent surface of the cartridge where the cells are immobilized is needed, while reducing the volume of the added probe. This method is obtained by the following:
1. Inserting an object inside the cartridge to reduce the volume.
2. Using a volume that is large enough, but smaller that the 320 microliters across the entire surface where the cells are immobilized when the cartridge is in a horizontal position and the surface with the cells is downside (optical viewing surface on bottom).
3. Use a small volume plus a fluid with a density that is lower than the density of the reagents. The low density fluid floats on top of the reagent and allows the reagents to spread uniformly across the entire surface.

Figure 7:
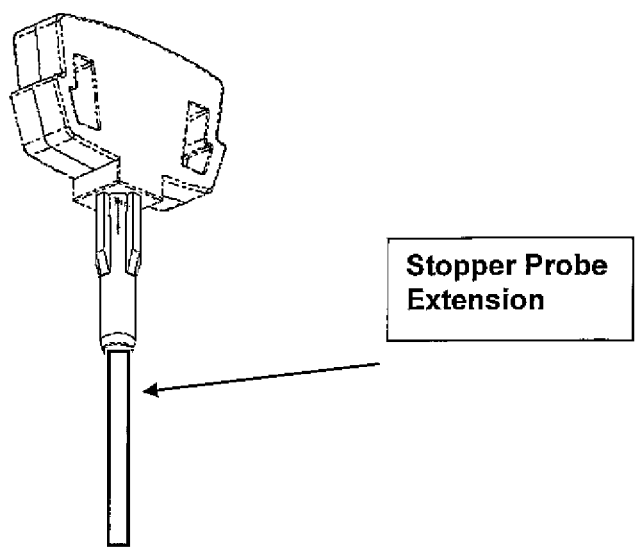
FIG. 7: Schematic representation of the stopper with probe extension for FISH cartridge for reducing the chamber volume of the cartridge.

As an example of the first possibility, an extension is introduced at the probe end of the stopper so that a portion extends the full length of the chamber (FIG. 7). The extension consumes approximately ⅓ of the volume of the chamber. The extension diameter is dimensioned such that it will slide through the chamber opening, 2.36 mm diameter. The extension is made by molding an entire new plug over the molding on the existing plug, or inserting a solid metal rod through the center line of the plug. The material must be inert to the reagents as, for example, 316 stainless steel, polypropylene or Inconel 625. The over molding of the upper portion of the plug with a thermal plastic is necessary to ensure the proper plastic durometer for maintaining shape during insertion and when positioned in the chamber to maintain liquid seal and locking of the plug. Further, the plug and extension optionally has an access hole through the center for monitoring temperature within the chamber during processing. The plug is further designed to be removed and re-used after proper cleaning.

Figure 8:
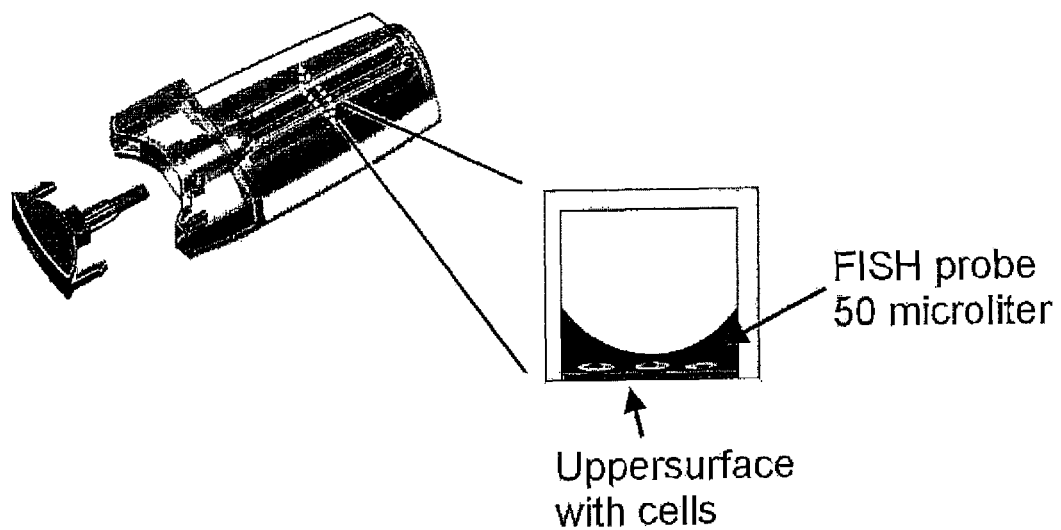
FIG. 8: Schematic representation of the cartridge. A cross-sectional illustration depicts the cartridge inverted with die location of the cells and FISH reagents illustrating a low reagent volume distribution the lower face of the chamber, thus allowing enough reagents to only cover the cells along entire lower surface.

A second embodiment is depicted in FIG. 8. A volume of 50 microliters of FISH reagents is sufficient to cover the whole upper surface of the cartridge. This volume needed to ensure complete reactions and is dependent on the viscosity and hydrophobicity of the reagents. After addition of the reagents, the cartridge is placed in a horizontal position to further ensure exposure to the reagents.

One other embodiment incorporates the second embodiment with a further reduction in reagent volume. After injecting of the reagents as described, an extra fluid with a lower density is injected. As the lower density fluid floats on top of the reagents of the reagents, there is a more complete reaction over the entire surface. Depending on the components of the reagents, a volume of 25 microliters reagents is obtained.

Reanalysis of Immunomagnetically-Labeled Cells

Chromosomal aneuploidy is associated with genetic disorders, particularly cancer. Diagnostic methods are available that provide for the detection of these chromosomal abnormalities particularly with the use of in situ hybridization (ISH). The application of ISH and immunocytochemistry (ICC) on tissue or cell samples has been well established, but there is a clear need to establish a diagnostically effective method for the simultaneous analysis of ISH and ICC on a single cell. One aspect of the present invention provides for the detection of these chromosomal abnormalities on individual cells as they relate to the confirmation of morphologically suspect cancer cells through a cost effective and highly specific means.

One aspect of the present invention provides for the further processing of rare cells after enrichment and immunocytochemical (ICC) analysis. For example, circulating rare cells such as epithelial cells are identified as suspect cancer cells (U.S. Pat. Nos. 6,365,362; 6,645,731; and U.S. Ser. No. 11/202,875 are incorporated by reference). Suspect cells are identified through specific cellular antigens and nucleic acid labeling. Confirmation of these suspect cells are subsequently determined by the expression of specific unique target sequences, defining either a chromosome and/or gene, used to assess chromosomal changes (i.e. aneuploidy) within the identified suspect cell. Accordingly, one embodiment of the present invention includes the combination of ICC staining and subsequent conformation by fluorescent in situ hybridization (FISH) on a group of selected chromosomes which define a CTC.

The cancer confirmatory assay provides an increased specificity after immunomagnetic enrichment and fluorescent imaging of circulating tumor cells as provided by the CellTracks® AutoPrep® and CellTracks® Analyzer II Systems (Immunicon Corporation) and further described in U.S. Pat. No. 6,365,362. A confirmatory test permits the designation of 1 or more CTC's as a cancer cell regardless of the stage of the disease and thus lowers the threshold for calling a sample positive for CTCs. One embodiment of the present invention is assessing aneuploidy in chromosomes 1, 7, 8 and/or 17 to confirm ICC-determined suspect CTC's. A further embodiment includes the detection of individual genes such as, but not limited to, HER-2, IGF-1, MYC, EGFR, and the androgen receptor (AR) to detect the presence or absence of therapeutic targets and thus provides a means to make the correct choice of treatment.

Accordingly, an automated and standardized method for blood sample processing provides identification of circulating epithelial cells by ICC. Aspirated plasma from a partitioned blood sample is combined with a ferrofluid reagent conjugated to antibodies specific for a target cell population (i.e. EpCAM positive). These cells are immunomagnetically collected through an externally applied magnetic field, allowing for separation and removal of unlabeled cells.

Once the target cells are separated, they are dispensed into a disposable cartridge for image analysis using an image presentation device (U.S. Pat. Nos. 6,790,366 and 6,890, 426). The device is designed to exert a magnetic field that orients the labeled cells along the optically transparent surface of the chamber for subsequent ICC imaging.

After ICC imaging, suspect cells are identified using appropriate algorithms. Images of the suspected cells are presented to the user who makes the final decision about the identity of the presented suspect cells. Images of the suspect cells and their relative position along the optically transparent viewing surface of the chamber are recorded and archived for later use. Since ICC imaging alone lacks the specificity to assess the clinical significance of blood samples with less than 5 CTC's or to provide detailed genetic information about suspected cancer cells, subsequent analysis using multiparametric genetic profiling on individual suspect cells is needed to provide a complete profile and establish a confirmatory mechanism that can be used in diagnostic analysis, including screening, assessing recurrence of disease, and overall survival. One embodiment of the present invention utilizes fluorescent in situ hybridization (FISH) as a multiparametric genetic analysis, but other profile assessments are considered. This provides both phenotypic and genotypic profile assessment for an individual cell present along the viewing surface FISH requires temperatures above the melting temperature of DNA as well a reagents that are not compatible with the ICC labeling. Most of the ICC and DNA labels do not survive the FISH procedure with any signals lost in processing. Thus, a cell that was identified as being an interesting cell for FISH analysis can not be traced back on its position. Therefore there is a need to have a detection method that once the ICC image is obtained, the cell position along the optically transparent viewing surface is maintained for subsequent multiparametric genetic analysis (FISH) or other types of analysis in which the ICC labels are lost. This is achieved, in part, by fixing the cells on the optically transparent surface after the ICC image is obtained without a loss of cells or any substantial movement along the surface. Accordingly after addition of the FISH reagents, the cartridge is placed on a hotplate having the surface with the immobilized cells in contact with the hotplate. Depending on the type of assay the hotplate is programmed with different temperature cycles that run between 2 and 48 hours. After the temperature cycles are completed, the excess FISH reagents are removed from the cartridge. The cartridge is filled with a buffer solution containing a DNA label to visualize the nuclei of immobilized cells. Depending on the DNA label used, the label remains in the cartridge or is washed out of the cartridge after staining.

Next, the cartridge is placed back in the CellTracks® Analyzer II System for a second scan. Because cells present on the upper surface during the first ICC image analysis were immobilized, the same cells are still in the same relative location inside the cartridge. To assess the shift of the cartridge relative to the imaging system (CellTracks® Analyzer II System), the locations of the nuclei in the images of the second scan are compared to the location of the nuclei in the images of the first ICC scan. The shift of these images with respect to each other is determined using convolution algorithms. After this shift has been determined a specific cell of interest, based on its ICC image, can be selected from a list and be relocated on the surface of cartridge after FISH in the second scan. Next fluorescent images of the different FISH probes are acquired.

Figure 9:
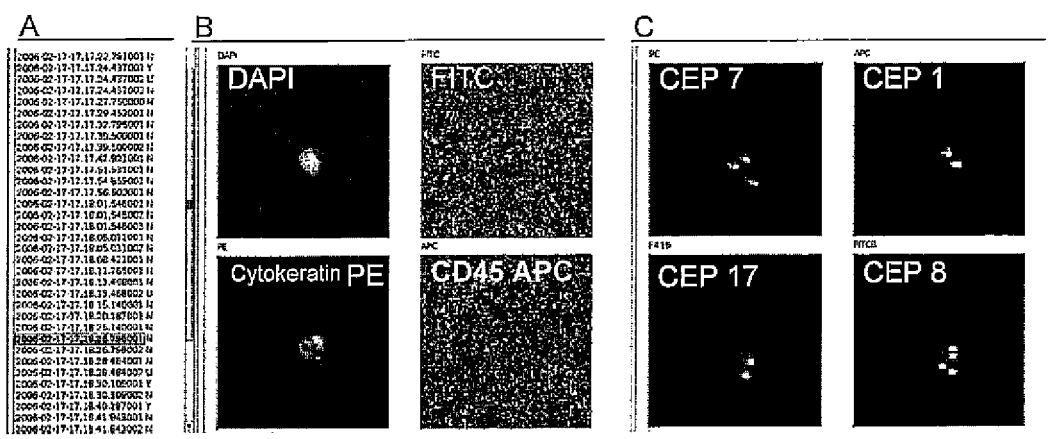
FIG. 9: Representative image of a tumor cell initially identified through immununocytochemisty (ICC) with subsequent FISH analysis for the presence of chromosome 1, 7, 8 and 17. Panel A shows a list of CTC candidates identified by the software on basis of their ICC signature. Panel B shows the acquired fluorescent ICC images acquired. Panel C shows the corresponding FISH signals for chromosomes 1, 7, 8 and 17 demonstrating the aneuploid signature of the same cell tumor cell.

FIG. 9 shows a representative image of a tumor cell, identified by ICC and probed for the presence of chromosome 1, 7, 8 and 17. Panel A shows a list of CTC candidates identified by the software as cytokeratin (cytoskeletal protein present in cells of epithelial origin) positive and DAPI (nucleic acid stain) positive. The corresponding images of the highlighted event were identified as a CTC by the user as it confirmed the CTC definition (cytokeratin positive, CD45 negative, DAPI positive event with the morphological appearance of a cell). Four images taken with a 10× objective are shown in Panel B. The The top left image shows the DAPI staining of the nucleus and the bottom left image the cytokeratin staining of die cytoplasm. CD45 staining and FITC staining are lacking as illustrated by the lack of positive staining. After the cells were preserved and probed for the centromeric probes for chromosome 1, 7, 8 and 17, images of the upper surface of the cartridge were reacquired and the fluorescent signals of the probes for chromosome 1, 7, 8 and 17 are shown in Panel C for the same cell shown in B. Two copies of chromosome 1, three copies of chromosome 7, four copies of chromosome 8 and two copies of chromosome 17 are clearly visible demonstrating that the cell is aneuploid and confirming that the cell indeed is a cancer cell.

Figure 10:
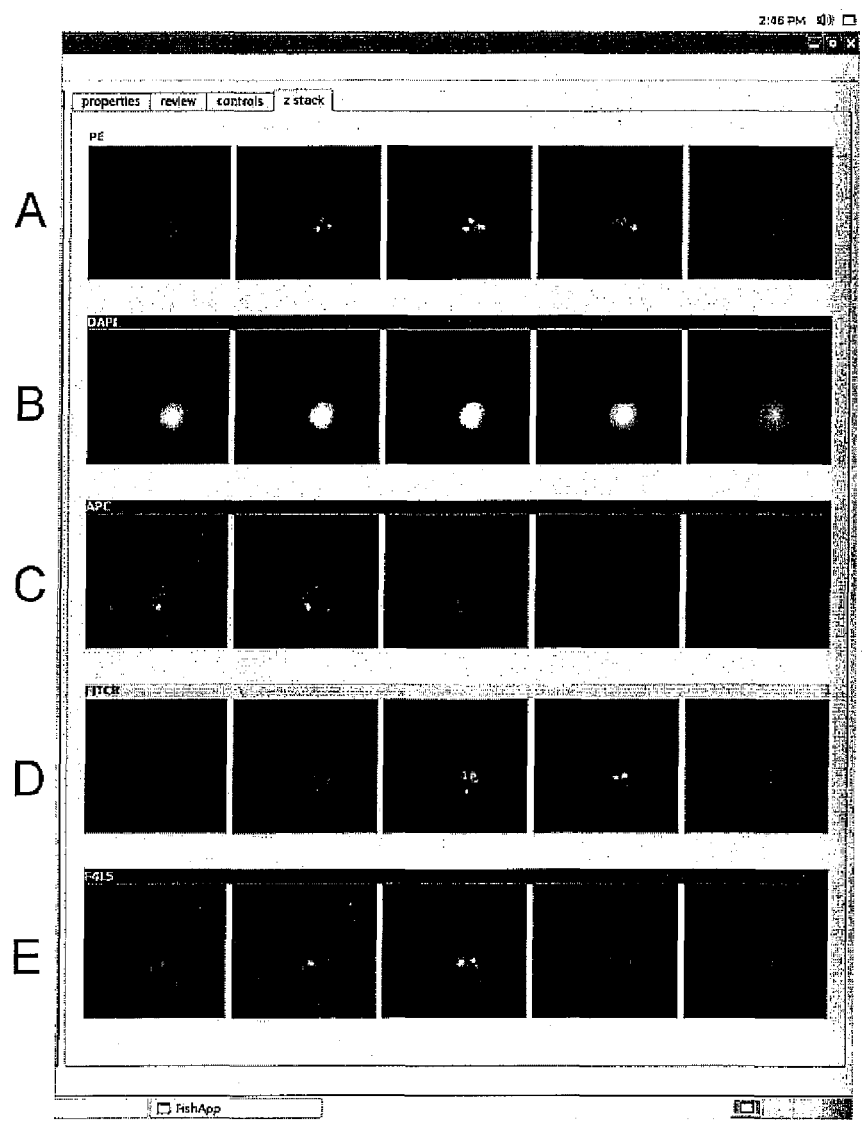
FIG. 10: Shown are five fluorescence images at different focal planes through the cell using excitation/emission filters for 5 different fluorochromes. Panel A shows the images for a cell using PE. Panel B shows images for the same cell using DAPI. Panel C shows images for the same cell using APC. Panel D shows images for the same cell using FITC. Panel E shows images for the same cell using Dy415.
Figure 11:
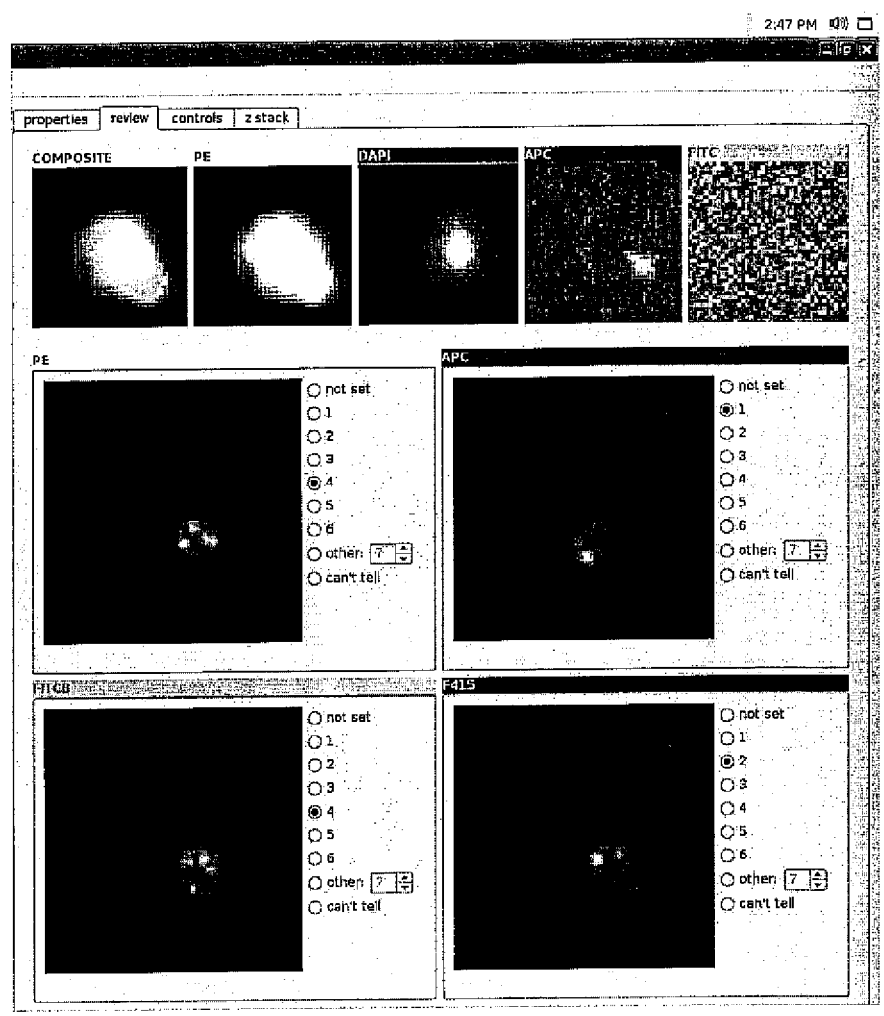
FIG. 11: Results from ICC and FISH analysis to confirm a CTC. Panel A shows ICC images of the ICC scan on which a suspect CTC was identified. Panel B shows the corresponding fluorescence signals, using FISH probes. Corresponding counts of the signals for each probe are shown next to each image; 4 count for PE, 1 count for APC, 4 count for FITC and 2 count for Dy415.

Images displayed in FIG. 10 are acquired using a 10×, NA 0.5 plan achromat objective. Although the resolution is sufficient for most centromeric probes, it is not sufficient for the gene specific probes, for example BER-2 and EGFR FISH probes. For this reason the 10×, NA 0.5 objective, the objective used for ICC image acquisition, is replaced by a 40×, NA 0.6 objective, corrected for the optical thickness of the transparent upper surface of the cartridge. The use of high NA objectives allows for 3D imaging of the cell of interest allowing for a confident determination of the correct number of copies for FISH probe labeled sequence in a selected cell. Multiple images at different focal planes along the optical axis of a specific cell of interest are acquired followed by 3D reconstruction of the cell. FIG. 10 shows 5 such slices through the cell using excitation/emission filters for 5 different fluorochromes. In Panel A, five slices for PE are shown. In slice #2, only two signals are visible whereas in slice #3 three signals are visible. Panel B shows 5 slices of the DAPI staining. In the APC slices of Panel C, #2 slice shows 1 signal. In the FITC slices of Panel D, slice #3 shows two signals and slice #4 shows two different signals, making the total for this probe 4. In Panel E, Dy415 slices show 1 signal in slice #2 and two signals in slice #3. From the images, it is clear that the probes are located in different parts of the nucleus and that using only one focal plane the counting of the signals would not be correct. In FIG. 11 Panel A fluorescence ICC images of the CTC, presented as a stack of images from FIG. 10. In panel B, the slices for each fluorochrome are added and the average intensity is presented thereby scaling the images to use the fall range of intensity levels which facilitates enumeration. The count for the number of signals with each probe are shown next to each image (i.e. 4 for PE, 1 for APC, 4 for FITC and 2 for dy415).

It is understood that the subject matter of this invention is not limited to the detection of cancer cells but can also be used to characterize other cell types. One cell type frequently pursued for detection of cytogenetic abnormalities is fetal cells in maternal blood. To enrich for such cells, markers need to be targeted that are present at high frequency on the fetal cells and in low frequency on the maternal cells. One cell type that is frequently pursued is the nucleated red blood cells. A marker that is present on all nucleated red blood cells is, for example, the tranisferhi receptor (CD71). When coupled to ferrofluids, nucleated red blood cells are reproducibly enriched from whole blood with the CellTracks® Autoprep® System. The enriched cells contain fetal nucleated red blood cells, maternal nucleated red blood cells, activated T-lymphocytes, immature reticulocytes and other cells that have been carried over by the immunomagnetic enrichment. The enriched cell population is now be stained with markers that discriminate between cells of fetal and maternal origin. One such panel of markers is the use of CD45 to eliminate leukocytes from the analysis in combination with Hemoglobin F that is present in fetal red blood cells but only rarely in maternal red blood cells, carbonic anhydrase that is only present in adult red blood cells and DAPI to identify the nucleus of the cells. The CellTracks® Autoprep® System is used to stain tie cells in a reproducible manner. As some of the antigens are intracellular the cells, cells need to be permeabilized for the antibodies to pass the cell membrane. The agents used for permeabilization also lyse the immature reticulocytes, specifically selected by the use of CD71 and the remaining erythrocytes that were carried over through the procedure. After the staining of the cells with the probes that have different reporter molecules, the cartridge containing the stained cells are placed in the CellTracks® Analyzer II System. The system identifies fetal nucleated red blood cell candidates as $DAPI^+$, $CD45^-$, Fetal $Hemoglobulin^+$, Carbonic $Anhydrase^-$ events. The user can confirm that these events indeed have all the characteristics typical for fetal nucleated red blood cells. After the system remembers the location of the fetal nucleated red blood cells, the cartridge is emptied as described above and the cells are hybridized with probes for cytogenetic analysis. Probes that are typically used to identify relatively frequent cytogenetic abnormalities are those that recognize chromosome X, Y, 13, 18 and 21. After the cells have been stained, the cartridge is reinserted hi the CellTracks ® Analyzer II System, because the cells that were present on the upper surface during the first ICC image analysis were immobilized the same cells are still on the same location inside the cartridge. The system returns to the events and takes images of the fluorochromes used to identify chromosomes X, Y, 13, 18 and 21. The user than assesses whether the copy number of each of the chromosomes and determines the sex of the fetus and whether or not the copy number of the chromosomes suggest the presence of cytogeonetic abnormalities.

EXAMPLE 1

Detection of Cytogenetic Aberrations after CTC Identification

CTCs from 7.5 mL of blood were identified as cytokeratin+, CD45− nucleated cells after immunomagnetic enrichment targeting the EpCAM antigen using the CellSearch System (Veridex, LLC). CTCs are identified by the CellTracks® Analyzer (Immunicon Corporation) where the cells are magnetically held along the upper surface of a cartridge. For cytogenetic analysis, the fluid in the cartridge was removed and the cells fixed while maintaining their original position. Fluorescently labeled probes for chromosome 1, 7, 8 and 17 were introduced into the cartridge and hybridized to the cells. The fixation and hybridization process removes the fluorescent labels used for CTC identification. After hybridization the cartridges were again placed on the CellTracks® Analyzer and analyzed for a second time. The fluorescent images of the CTC's identified in the first scan are then combined with the fluorescent images from each of the four chromosomes labels obtained in the second scan. The number of chromosomes 1, 7, 8 and 17 were enumerated for each CTC that was identified in the first scan. The number of chromosomes detected in leukocytes that surrounded the CTC's were used as internal controls. In 7.5 mL of blood from 8 patients with metastatic carcinoma, 1 to 7 CTC's were identified. Greater than or less than two copies of chromosome 1, 7, 8 or 17 were detected in all 8 patients. Heterogeneity in the chromosomal abnormalities were not only detected between CTC's of different patients but also among CTCs of the same patient. Of the 21 CTCs examined, 77% showed chromosomal abnormalities and a majority showed an increase in the number of copies of the chromosomes. In contrast, more than 80% of the leukocytes examined showed two copies of the chromosomes and none showed an increase in chromosome copy number. Conclusions: Cytogenetic composition of CTC's can be assessed after they have been identified. The presence of aneusomic CTC's provides information to the outcome of patient conditions and provides a prognostic indicator of clinical outcome. Further, gene alterations in CTC's provide indices to current and future cancer therapies.

EXAMPLE 2

Evaluation of Anti-Cancer Targets on CTC's to Predict Therapeutic Success

The CellSearch System™ has been used in multi-center prospective studies to demonstrate that presence of tumor cells in blood of patients with metastatic carcinomas is associated with poor survival prospects. Failure to eliminate Circulating Tumor Cells (CTCs) after one cycle of therapy in these studies strongly suggests that these patients are on a futile therapy. Assessment of the presence of therapeutic targets on the tumor should enable the appropriate choice of therapy. Anti-cancer targets are identified on CTCs before initiation of therapy. Cells from 7.5 mL of blood are identified as cytokeratin(CK)+, CD45− and nucleated after EpCAM immunomagnetic selection. Suspect CTCs are identified and localized at the upper surface of a cartridge where they are held by a magnetic field. Fluorescently labeled antibodies that recognize treatment targets associated with known therapies such as HER2, IGF-1, Bcl-2 and EGFR are assessed on the CTCs. Subsequently, CTCs are preserved for cytogenetic analysis. After the fluid in the cartridge is removed, the cells are fixed and maintain their original position for probe hybridization. Since the system knows their original position, the cells can be reexamined for the presence of probes of interest. The results show a CTC and a leukocyte before and after hybridization with chromosome 1, 7, 8 and 17.

We claim:

1. A system for the detection and enumeration of suspect target cells in a mixed cell population, comprising:
   a. means for obtaining a biological specimen from a test subject, said specimen comprising a mixed cell population suspected of containing target cells;
   b. means for isolating a subpopulation of suspect said target cells by immunomagnetic enrichment using colloidal magnetic particles;
   c. means for identifying suspect target cells by a phenotypic profile analysis means wherein a magnetic holding force holds said target cells for imaging;
   d. means for preparing suspect target cells identified by the means of step c for a genotypic profile analysis means wherein shear forces to replace preparatory buffers on the target cells are less than the magnetic holding forces required to maintain the target cells for imaging; and
   e. means for confirming suspect target cells by said genotypic profile wherein said individual suspect target cell contains both phenotypic and genotypic characteristics.

2. The system of claim 1 wherein said means for obtaining a biological specimen includes fixation of said specimen.

3. The system of claim 1 wherein said phenotypic profile analysis is automated immunofluorescent cell analysis means.

4. The system of claim 1 wherein said genotypic profile analysis means is FISH wherein probes used in said FISH are repeat-depleted.

* * * * *